United States Patent [19]

Schwartz et al.

[11] 4,046,150

[45] Sept. 6, 1977

[54] MEDICAL INSTRUMENT FOR LOCATING AND REMOVING OCCLUSIVE OBJECTS

[75] Inventors: Robert S. Schwartz, Boulder; Ronald R. Pfister, Littleton, both of Colo.

[73] Assignee: American Hospital Supply Corporation, Evanston, Ill.

[21] Appl. No.: 596,811

[22] Filed: July 17, 1975

[51] Int. Cl.² .................................................. A61B 17/22
[52] U.S. Cl. .................................................. 128/328
[58] Field of Search ..................... 128/328, 350 R, 356

[56] References Cited

U.S. PATENT DOCUMENTS

| | | | |
|---|---|---|---|
| 1,612,697 | 12/1926 | Cecil | 128/356 |
| 1,677,671 | 7/1928 | Councill | 128/328 |
| 2,227,727 | 1/1941 | Leggiadro | 128/328 X |
| 2,918,919 | 12/1959 | Wallace | 128/328 |
| 2,943,626 | 7/1960 | Dormia | 128/356 X |
| 3,189,031 | 6/1965 | Andersen | 128/350 R |
| 3,334,630 | 8/1967 | Kramer | 128/328 |
| 3,413,976 | 12/1968 | Roze | 128/328 |
| 3,830,240 | 8/1974 | Antonevich et al. | 128/328 |

*Primary Examiner*—Channing L. Pace
*Attorney, Agent, or Firm*—Tilton, Fallon, Lungmus, Chestnut & Hill

[57] ABSTRACT

An instrument particularly useful for locating and removing ureteral calculi and other occlusive objects from body passages. The instrument includes a flexible tube or sheath which slidably receives a tightly-twisted multi-stranded cable of a length greater than that of the tube, the cable having an integral cage portion at its distal end. That cage portion, which is normally collapsed and concealed within the distal end of the tube, may be extended beyond the tube to assume an expanded helical pear-shaped configuration for ensnaring and withdrawing ureteral stones and other passage-occluding bodies. The tightly wound strands of the cable are arranged in a circumferential pattern about an axial lumen which in one embodiment is useful for fluid drainage and injection and which in other embodiments accommodates conductors for transmitting light, images, and/or ultrasonic energy. The sheath or outer tube of the instrument is transparent, thereby permitting visual inspection of the spirally-wound cable slidably disposed therein. Suitable markings on the cable, visible through the transparent wall of the sheath, indicate the extent of insertion of the instrument during an operative procedure. The instrument also includes a handle for extending and retracting the cage, and suitable means for generating and transmitting light and ultrasonic waves.

14 Claims, 9 Drawing Figures

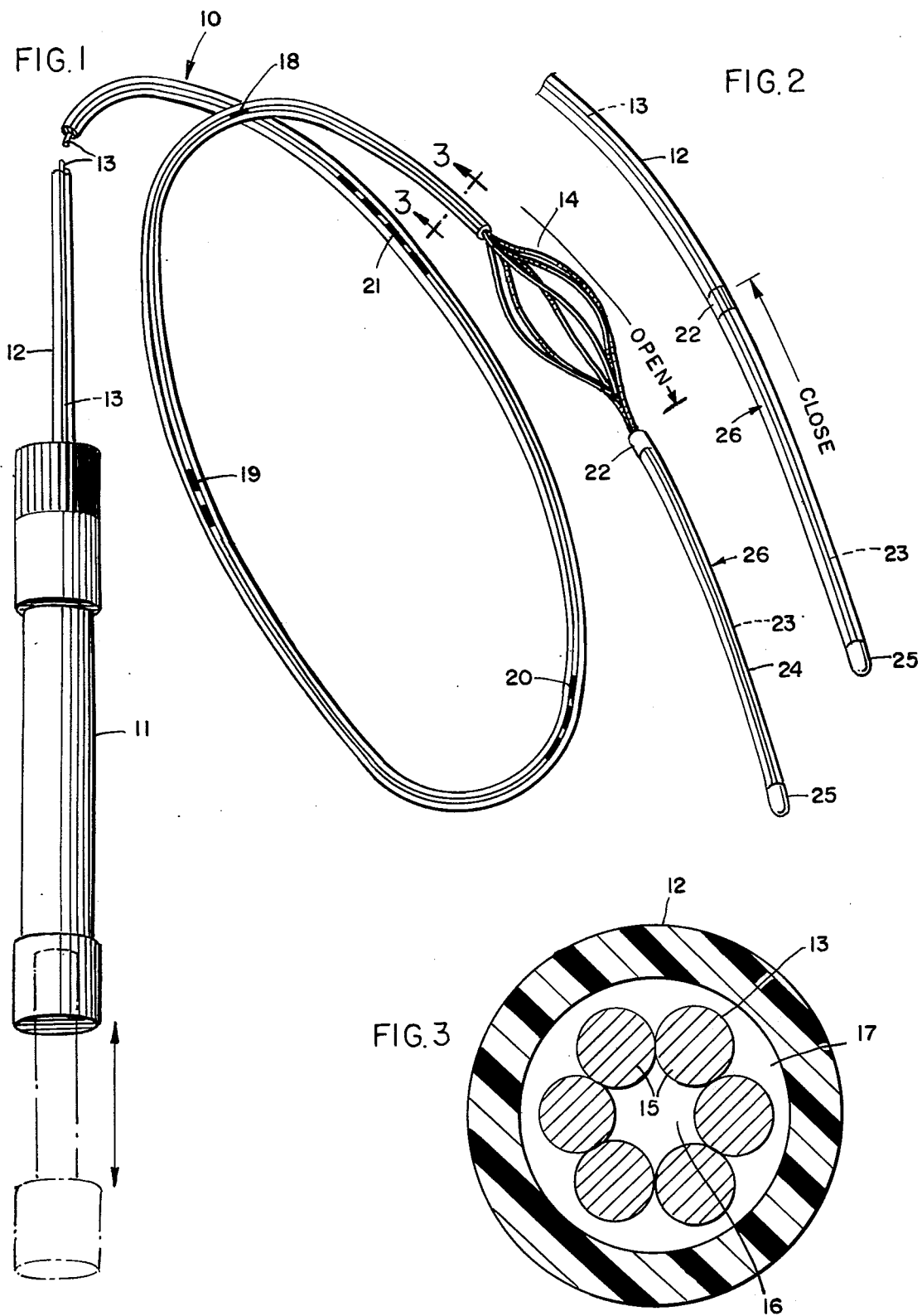

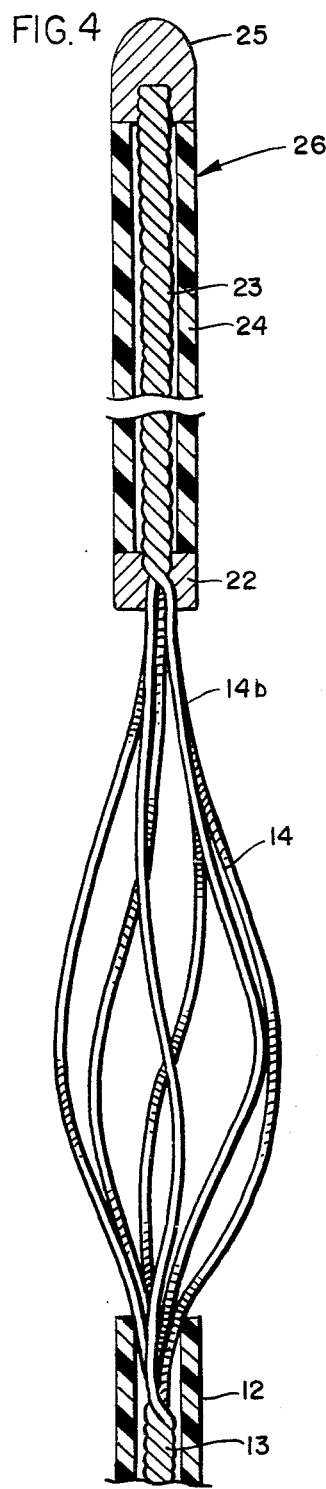
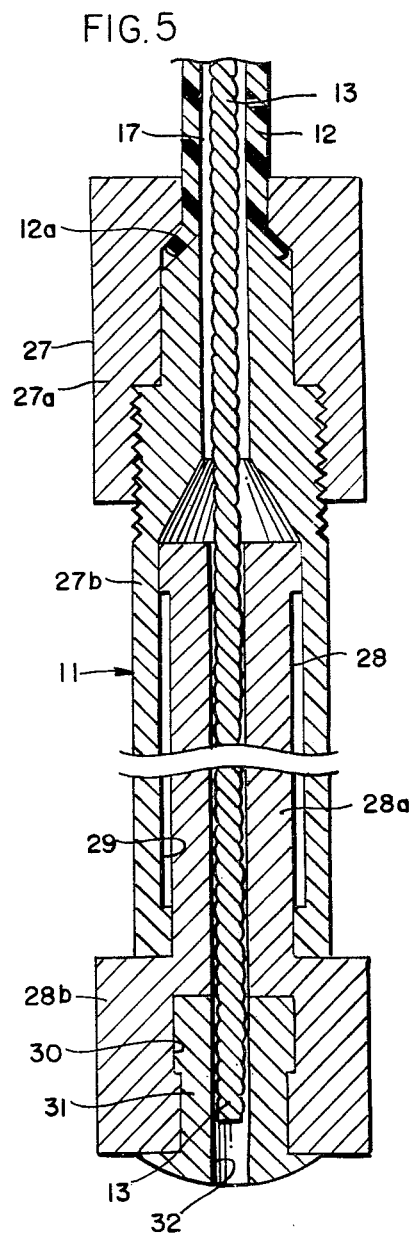
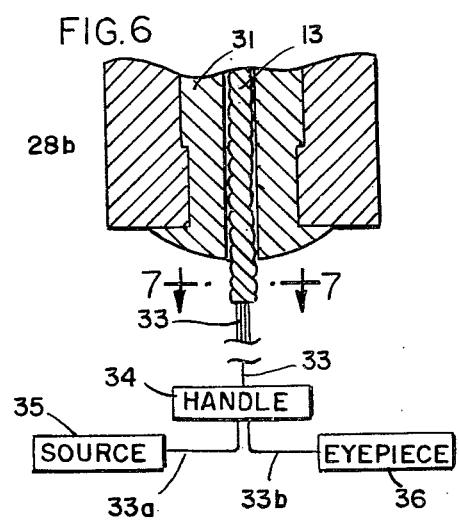
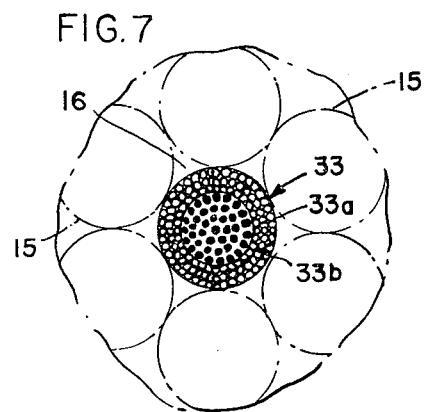
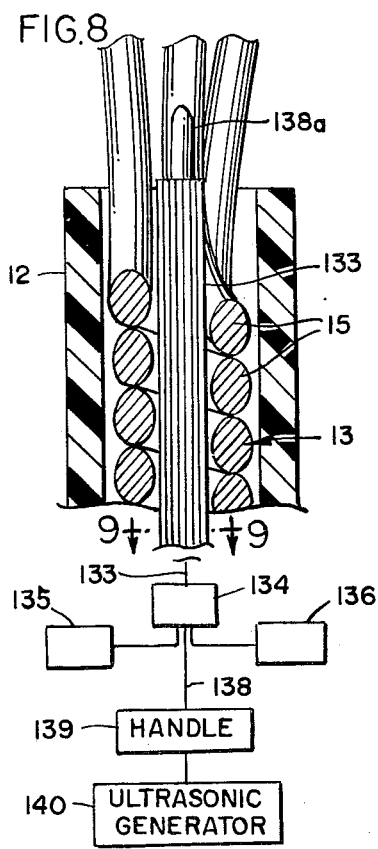
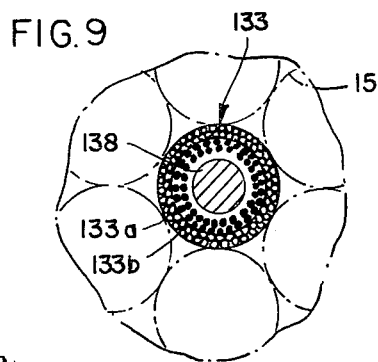

4,046,150

MEDICAL INSTRUMENT FOR LOCATING AND REMOVING OCCLUSIVE OBJECTS

BACKGROUND

Techniques and instrumentation for the cystoscopic removal of ureteral calculi have been well documented in the medical literature and perhaps to a lesser extent in patent literature. Although procedures have varied, most of them have involve dilatating, anesthetizing and lubricating the ureter and then attempting to grasp the calculus and either crush it or drag it out. One such early device, disclosed in Cecil U.S. Pat. No. 1,612,697, took the form of a flexible tubing through which at least a pair of wires extended, the wires being formed at their distal ends to define a basket or cage for ensnaring ureteral calculi. Shortly thereafter, Vose modified the Cecil instrument to provide a cage composed of four wires, such wires spreading to form the cage, upon emergence from the tube, because of the natural springiness of those wires. (N.E.J. of M., Vol. 198, No. 12, 638–639 (1928)). Somewhat similar instruments were developed by Councill, Johnson, Morton, and others. (Jour. A.M.A., 1907–1909 (1926); J. Urol., Vol. 37, 84–89 (1937); J. Urol., Vol. 60, 242–243 (1948); Councill U.S. Pat. No. 1,677,671). More recent variations have included spiral extractor configurations to promote effective grasping and withdrawal of the calculi (Jour. A.M.A. Vol. 114, pp. 6–12 (1940); J. Urol., Vol. 40, 83–100 (1938); Dormia U.S. Pat. No. 2,943,626).

Although ultrasound is rapidly finding increasing use in medicine, its use in the genitourinary tract has mainly been limited to examination of renal and bladder lesions. Lamport and Newman may have been the first to consider ultrasonic lithotresis, successfully performing laboratory experiments in breaking or disintegrating stones in the ureters of dogs and cadavers (Yale J. Biol. Med. Vol. 27, 395 (1955); J. Urol. Vol. 70, 704 (1953)). In 1973, Goodfriend published the first successful ultrasonic disintegration and removal of an impacted ureteral stone from a patient (Urology, Vol. 1, No. 3, 260 (1973)).

SUMMARY

This invention is concerned with an improved instrument which is especially effective for locating, ensnaring, and removing occlusive bodies from the ureter, or from other ducts and vessels, and which overcomes some of the shortcomings and disadvantages of prior instruments intended for the same purpose.

The improved device includes a smooth flexible sheath or tube through which a cable or tightly-twisted strands or filaments extend. The cable has a length which exceeds that of the sheath and, at the cable's distal end, the strands are formed to define a collapsible cage or basket. The filaments or wires of the cage are helically curved and the cage as a whole has a distinctive pear-shaped outline, large at the proximal end to faciliate calculus entry and smaller at the distal end to help preclude calculus escape once captured. It has been found that less force is required to spread adjacent wires at the enlarged proximal end of the cage and that greater force is required to spread the wires at the reduced distal end — a distinct advantage in capturing calculi and preventing escape once a calculus has entered the center of the cage.

The sheath is transparent and has an inner diameter substantially greater than that of the twisted cable disposed therein. Markings on the cable at selected points along its length are visible through the sheath's transparent wall to provide a precise indication of the extent of insertion of the instrument regardless of the extended or retracted condition of the cage. Because of the annular spacing between the cable and sheath, and the transparency of that sheath, slight lurching or flexing movement of the cable within the sheath as a stone or other body is captured, and changes in the rotational movement of the cable within the sheath under such conditions, serve as visual indications of the operation of the device.

A particularly important aspect of the invention lies in the fact that the tightly wound strands of the cable are arranged in a circumferential pattern defining a central lumen which extends the full length of the cable from the wire cage to (and, if necessary, beyond) the operating handle. The lumen therefore provides a passage for the drainage of fluid and the injection of dyes, medicaments, and other liquids. The lumen may also be used to receive conductive elements such as light-transmitting fibers and/or an ultrasonic wave-transmitting line. The ultrasonic line is slidable within the lumen of the cable so that it may be shifted into direct contact with a stone or other body ensnared within the cage. Such direct contact promotes effective operation of the conductor, permitting acoustic waves to be transmitted directly to a stone in order to shatter it, and also helps to retain the stone within the cage. The cage thus serves as a stop to brace the stone or other occlusive body against movement in response to direct contact by the conductive element.

Other advantages and objects of the invention will be apparent from the specification and drawings.

DRAWINGS

FIG. 1 is a perspective view of an instrument embodying the invention, the instrument being illustrated with its cage in expanded and extended condition.

FIG. 2 is a fragmentary perspective view showing the distal portion of the instrument with the cage in retracted and collapsed condition.

FIG. 3 is an enlarged cross sectional view taken along line 3—3 of FIG. 1.

FIG. 4 is an enlarged fragmentary longitudinal sectional view showing the distal portion of the instrument with the cage in expanded condition.

FIG. 5 is an enlarged longitudinal sectional view showing the proximal portion of the instrument as depicted in FIG. 4.

FIG. 6 is a fragmentary longitudinal sectional view showing the proximal end of the instrument of FIG. 5 with the addition of light transmitting elements through the lumen of the cable, such light transmitting elements, and the generating and receiving means therefor, being illustrated in schematic fashion.

FIG. 7 is an enlarged cross sectional view taken along line 7—7 of FIG. 6.

FIG. 8 is a fragmentary longitudinal sectional view, partly schematic, illustrating a further embodiment of the invention.

FIG. 9 is an enlarged sectional view taken along line 9—9 of FIG. 8.

DESCRIPTION

Referring to FIGS. 1-5, the numeral 10 generally designates an instrument comprising a handle 11, an elongated flexible tube or sheath 12, and a cable 13 extending through the sheath. The cable has a length substantially exceeding that of sheath 12 and near its distal end is formed to provide an integral and collapsible cage or basket 14.

The cable is composed of multiple strands or filaments 15 which are wound or twisted into tight circumferential and longitudinal engagement, as shown most clearly in FIGS. 3-5. The mono-layer of filaments defines a central lumen or passage 16 which extends the length of the cable from basket 14 to ( and, if necessary, through) handle 11. It will also be observed that the outer dimensions of the cable, as defined by a line circumscribing filaments 15, are substantially smaller than the inside dimensions of sheath 12. Consequently, an annular space 17 exists between the outer surface of the cable and the inner surface of the sheath.

Particularly effective results have been achieved with a cable having six strands or filaments as shown, although it is conceivable that a greater number, and perhaps a smaller number, might also be used. The filaments are preferably formed of wire (i.e., metal) and are flexible, corrosion resistant, and have high spring efficiency. A cobalt-nickel alloy marketed under the brand name "Elgiloy" by American Gage & Machine Company, Elgin, Illinois has been found especially suitable; however, other materials having similar properties might be used.

Sheath 12 is formed of a transparent plastic material which is flexible, durable, physiologically compatible, heat, moisture and corrosion resistant, and has low coefficients of static and kinetic friction. Heat resistance is essential where autoclavability is required. While various plastic materials might be suitable, fluorinated hydrocarbons (such as Teflon resin marketed by E.I. duPont deNemours & Co., Wilmington, Delaware) are believed particularly appropriate. The term "transparent" is used herein to refer to materials which have sufficient clarity to permit visual inspection of the cable through the wall of the sheath and is not meant to exclude materials which are more commonly regarded as being translucent but which in this context would have sufficient clarity to permit such inspection.

The transparency of the sheath is particularly important in connection with visual inspection of markings 18-21 applied to the cable at selected distances from cage 14. Each marking is distinctive; in the illustration given, the first marking consists of a single darkened segment 18, the second marking 19 consists of a pair of such segments, the third marking 20 consists of three such segments, and so on. The markings may be formed by applying dye or some other coating or impregnating material to the cable and, if desired, different colors may be used to distinguish each of the markings in the spaced series. It will be observed that such markings are protected by the transparent sheath and that they provide a means for accurately gauging the extent of insertion of the cable into a body passage regardless of relative cable-sheath displacement, that is, regardless of whether the wire cage is expanded or collapsed.

As shown most clearly in FIG. 4, cage 14 is generally pear-shaped in outline, having its widest dimension on the proximal side of the expanded cage's longitudinal mid point. The greater spacing between adjacent wires at the proximal end 14a of the cage facilities calculus entry while the smaller spacing at the distal end 14b helps to preclude calculus escape when captured. Also, the larger bulge (sharper curvature) at the proximal end results in lower force requirements for separating adjacent wires, while greater force is required to cause spreading of such wires at the more tapered smaller distal end. The spiral configuration of each cage wire also contributes in promoting entry of a stone into the cage from the proximal end thereof (because of a twisting action of the cage as it is pulled through the body passage) and in retaining a stone within the cage (because there is no straight longitudinal channel between the cage wires through which a calculus might escape, each cage wire having its proximal and distal end portions in non-collinear relation).

At the distal end of the cage wires are surrounded and secured by a connecting member in the form of ring 22. The outside diameter of the ring is no greater than (and preferably the same as) that of plastic sheath 12; thus, when the cage is collapsed within the distal end portion of the sheath, the outer surface of ring 22 is flush with the surface of the sheath or at least does not project laterally beyond the sheath's surface. In the form of the invention illustrated in the drawings, cable 13 continues in tightly twisted helical form for a substantial distance beyond ring 22, as represented by numeral 23 in FIG. 4. The elongated end portion of the cable is enclosed in a plastic tube 24, and a rounded terminal element 25 is secured to the extreme end of the cable. The terminal element 25, tube 24, cable end portion 23, and connecting element 22 all combine to define a filiform tip extension 26, the purpose of such an extension, as is well known in the art, being to facilitate reinsertion of the instrument if a calculus is not captured in the first retractive pass. For those surgeons preferring an instrument without a filiform extension, the twisted end portion 23 of the cable may be greatly reduced in length, tube 24 may be eliminated, and terminal element 25 may be positioned immediately adjacent ring 22 or, alternatively, the ring and terminal element may be unified in a single terminal connecting element having the general configuration of element 25. In any event, the terminal element is of the same diameter as sheath 12 and, where a filiform tip extension is provided, tube 24 is also of the same cross sectional dimensions as sheath 12. Tube 24 may be formed from the same flexible transparent tubular stock as sheath 12 and, if desired, the temper of the coiled end portion 23 of the cable may be reduced by appropriate treatment during the fabrication process so that the filiform tip extension may be bent by the surgeon into any selected configuration to facilitate insertion and use.

Handle 11 essentially comprises a cylinder 27 connected to the proximal end of sheath 12 and a plunger 28 secured to the proximal end of cable 13. In FIG. 5, it will be observed that the cylinder is composed of two parts 27a and 27b which are threadedly secured together and which securely clamp the flared proximal end 12a of the sheath. The plunger 28 has a stem portion 28a which is slidably received within a bore 29 of cylinder portion 27b. The plunger is provided with an enlarged operating knob 28b and, in the embodiment illustrated in the drawings, the knob is provided with a recess 30 which receives a plug 31, the plug being soldered, cemented, or otherwise permanently secured to the proximal end portion of cable 13.

When the knob 28b is urged forwardly (distally) to advance the stem portion 28a fully into bore 29, cage 14 is moved into its extended and expanded condition as illustrated in FIGS. 1 and 4. When retraction and collapse of the cage is desired, the knob is simply urged rearwardly (proximally) into the dotted line position shown in FIG. 1, the distal end of the instrument thereby assuming the appearance depicted in FIG. 2.

It will be noted from FIG. 5 that plug 31 is not closed at its end and, specifically, that the lumen of the cable (represented by numeral 16 in FIG. 3) is accessible for fluid injection or drainage of the handle's plug end. A radiopaque dye may thus be injected through the cable and into the area of cage 14 by inserting the tapered nose of a suitable syringe into opening 32 in cap or plug 31 and then expelling the fluid content of the syringe into the lumen of the cable. Thus, if the injection of dye into the ureter (or some other passage) is contemplated as part of the examination procedure, to be followed by a second entry into the ureter for stone removal, the present instrument, to the extent that it permit both objectives to be accomplished with only a single entry, reduces the effort, time, and risks of such operations.

The advantages of providing a drainage pathway are believed apparent. If desired, a suitable drainage tube can be coupled to the handle (plug) end of the plunger so that the fluid will be directed to a suitable receptacle (not shown). It is to be noted that one of the risks of manipulative stone removal using an instrument of this general type is that a stone might firmly resist removal after is has been captured within the instrument's cage. In such a case, a urologist may prefer to wait, sometimes as long as days, in hopes that the ureter might relax and allow the captured stone to be removed by the instrument; however, such a preferred course might not be available if flow through the ureter were completely blocked by the stone and device. In that event, abdominal surgery (laparatomy), sometimes on an emergency basis, would often be considered necessary. While use of the instrument of the present invention would not eliminate the need for such a laparatomy if the captured stone could not be withdrawn after a reasonable interval, the criticality of immediate action would tend to be reduced to the extent that the instrument could be left in place with the cable continuing to provide a drainage pathway until corrective surgery were performed.

FIGS. 6 and 7 illustrate a modified construction in which a fiber optics bundle 33 extends from cage 14 through the lumen 16 of the cable and completely through handle 11. The light transmitting bundle may be slidably disposed within the lumen so that the distal end of that bundle may be advanced into closer proximity to a stone (or other occlusive object) in the vicinity of cage 14. For that purpose, a handle 34, schematically illustrated in FIG. 6, may be secured to the bundle, the handle 34 being engagable with the proximal end of cable 13 (or with handle 11) to limit the extent to which the distal end of the fiber optics bundle may be extended into cage 14.

Except as used herein, the fiber bundle 33 may be entirely conventional. Certain of the light transmitting fibers, such as fibers 33a, are connected to a suitable light source 35. Other fibers of the bundle, such as fibers 33b, are connected to an eyepiece 36. Even if fibers 33b are not oriented or image-transmitting, the presence of a stone or other occulusive object in cage 14 would be discernible to an experienced operator because of a change (increase) in the intensity of reflected light. However, where a viewing of the operative procedure is considered necessary or desirable, fibers 33b may be oriented for the transmission of images to the eyepiece.

Since the fiber bundle 33 does not occupy the entire lumen 16, the advantages of visual inspection may be achieved without sacrificing the previously-described advantages of utilizing the lumen for fluid injection and drainage.

FIGS. 8 and 9 illustrate a further embodiment which is identical to the forms already illustrated and described except that the fiber optics bundle 133 is of annular cross sectional configuration, defining a passage 137 receiving a transmission line 138 for ultrasonic energy. Handle 134, light source 135, and eyepiece 136 function in the same manner as their counterparts 34-36 in the embodiment of FIGS. 6-7. The ultrasonic energy transmitting member 138 may be connected to a handle 139 so that the distal tip 138a of the member may be advanced into direct contact with a stone captured in cage 14. The opposite end of the energy conducting member is connected to an ultrasonic generator 140. Since the generation and transmission of ultrasonic waves are known and available to those skilled in the art, a detailed discussion of such components and their operation is believed unnecessary herein. Emphasis is placed herein on the combination of such elements with an expandable cage capable of holding a captured stone (or other occlusive object) in position so that it may be engaged by the distal tip of the ultrasonic conductor. Immobilization of the stone and direct contact between that stone and the conductor are important in achieving ultrasonic fragmentation or disintegration of the stone.

While FIGS. 8 and 9 disclose an instrument in which the lumen of cable 13 accommodates both light-conducting means and ultrasonic transmission means, it is to be understood that one or the other may be omitted. Thus, the acoustic transmission line or wire 138 may be disposed in lumen 16 without being surrounded by the fibers of tubular bundle 133 and, conversely, the tubular bundle may be disposed within the lumen without the additional presence of the ultrasonic transmission wire 138. In the latter case, the passage 137 of the tubular bundle 133 may be used advantageously in promoting fluid injection and drainage.

It is believed evident from the above that dimensions may be varied to a considerable extent in any instrument embodying this invention. However, for completeness of disclosure the following dimensions are given as having been found suitable for such an instrument: total length of instrument 10, 30 inches; length of filiform tip extension 26, 1.5 inches; outside diameter of sheath 12 and tubing section 24, 0.047 inches; outside diameter of wound cable 13 and cable tip section 23, 0.024 inches; length of cage 14 (i.e., distance between distal end of sheath 12 and ring 22 when cage is expanded), about 1.15 inches; diameter of cage 14 in expanded condition, about 0.63 inches; diameter of each strand or filament 15, 0.008 inches; radial measurement of annular spacing 17, about 0.002 inches; diameter of lumen 16, about 0.008 inches (enlarged to about 0.050 inches if light and/or sonic conductor positioned therein, with sizes of other components adjusted accordingly).

While in the foregoing we have disclosed embodiments of the invention in considerable detail for purposes of illustration, it will be understood by those skilled in the art that many of these details may be varied without departing from the spirit and scope of the invention.

We claim:

1. An instrument for use in locating occlusive objects in body passages and removing the same therefrom, comprising a flexible transparent tube having proximal and distal ends and having a passage extending longitudinally therethrough; a flexible cable extending through said passage; said cable including a collapsible cage portion and being slidable within said passage between a first position wherein said cage portion is collapsed and retracted within said passage at the distal end of said tube and a second position wherein said cage portion is expanded, extended, and exposed beyond the tube's distal end; and handle means connected to said cable at the proximal end of said tube for selectively shifting said cage between its retracted and extended positions; said cable having a lumen extending axially therethrough and communicating with said cage portion to provide a fluid pathway; said cable being composed of filaments twisted together between said cage and said handle means to provide a series of coils visible through said transparent tube.

2. The instrument of claim 1 in which said cable is longer than said tube.

3. The instrument of claim 1 in which said filaments are formed of spring wire.

4. The instrument of claim 3 in which said wire filaments are wound in tight engagement to form a single layer extending circumferentially about said lumen.

5. The instrument of claim 1 in which said cage portion is generally pear-shaped in outline when the same is extended, expanded, and exposed, said pear-shaped cage portion having an enlarged end facing proximally and having its widest dimension on the proximal side of the exposed cage's longitudinal mid point.

6. The instrument of claim 1 in which said cable is provided at selected points along the length thereof with surface markings visible through the transparent wall of said tube.

7. The instrument of claim 1 in which the internal diameter of said tube is substantially greater than the external diameter of said cable to provide an annular spacing therebetween.

8. An instrument for use in locating occlusive objects in body passages and removing the same therefrom, comprising a transparent flexible sheath having proximal and distal ends and having a passage extending longitudinally therethrough; a flexible cable composed of a plurality of wires extending uninterruptedly from one end of said cable to the other; said cable being slidably disposed in said passage of said sheath and having a length greater than said sheath; said cable including an integral cage portion slidable between a first position wherein said cage portion is collapsed and retracted within said passage at the distal end of said sheath and a second position wherein said cage portion is expanded, extended, and exposed beyond the sheath's distal end; and handle means connected to said cable at the proximal end of said sheath for selectively shifting said cage portion between its first and second positions; said wires being twisted tightly together between said handle means and said cage portion.

9. The instrument of claim 8 in which said cage portion is defined by said wires and has a pear-shaped configuration when expanded, extended, and exposed; said pear-shaped cage portion having an enlarged end facing proximally and a reduced end extending distally, and having its widest dimension on the proximal side of the exposed cage's longitudinal mid point.

10. The instrument of claim 9 in which a connecting member joins the wires at the distal end of said cage portion, said connecting member comprising a ring having a diameter no greater than the external diameter of said sheath.

11. The instrument of claim 10 in which said wires extend distally beyond said connecting member and are tightly twisted together to form an integral cable extension for a filiform tip.

12. The instrument of claim 8 in which said cable is provided at selected points along the length thereof with surface markings visible through said transparent sheath.

13. The instrument of claim 8 in which the internal diameter of said sheath is sufficiently greater than the external diameter of said cable to define an annular space therebetween.

14. The instrument of claim 8 in which said wires of said cable are wound into tight circumferential and longitudinal engagement to provide an annular arrangement of wires defining a lumen extending axially through said cable.